United States Patent
Borkow et al.

(10) Patent No.: US 6,710,077 B1
(45) Date of Patent: Mar. 23, 2004

(54) USE OF THIOCARBOXANILIDE DERIVATIVES FOR THE PREPARATION OF A MEDICAMENT FOR PREVENTING THE TRANSMISSION OF HIV TO UNINFECTED CELLS AND CONTRACEPTIVE COMPOSITIONS COMPRISING THE SAID DERIVATIVES

(75) Inventors: Gadi Borkow, Kfar Gibton (IL); Michael A. Parniak, Verdun (CA); Mark A. Wainberg, Montreal (CA)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 09/889,250
(22) PCT Filed: May 23, 1997
(86) PCT No.: PCT/US97/08838
§ 371 (c)(1),
(2), (4) Date: Dec. 8, 1998
(87) PCT Pub. No.: WO97/45116
PCT Pub. Date: Dec. 4, 1997

Related U.S. Application Data (60) Provisional application No. 60/040,380, filed on Mar. 10, 1997, and provisional application No. 60/018,668, filed on May 30, 1996.

(51) Int. Cl.[7] .................. A61K 31/34; A61K 31/38; A61K 31/05
(52) U.S. Cl. .................. 514/471; 514/448; 514/734
(58) Field of Search .................. 514/471, 448, 514/734

(56) References Cited

PUBLICATIONS

Balzarini et al, Antiviral Research, vol. 30(1), p. 30, XP002037331, May 19–24, 1996.*
Bruckheit et al, 124CA:219374, 1995.*
Makjovsky et al, "Inactivation of HIV by nonoxynol–9", The Lancet, Mar. 19, 1988, p. 645.*

* cited by examiner

Primary Examiner—Russell Travers
(74) Attorney, Agent, or Firm—Daniel Reitenbach (57) ABSTRACT

Method for preventing or inhibiting the transmission of HIV to susceptible uninfected cells by administering to the HIV, to cells infected with HIV, and/or to the uninfected cells, an effective amount of a compound of formula (I), wherein X is O or S, prior to the HIV or the cells infected with HIV, contacting the uninfected cells.

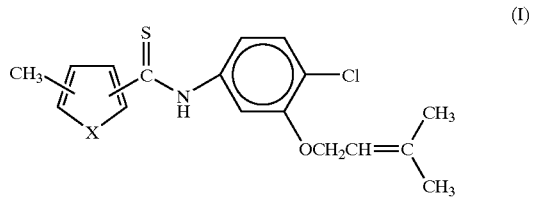

(I)

16 Claims, 7 Drawing Sheets

USE OF THIOCARBOXANILIDE DERIVATIVES FOR THE PREPARATION OF A MEDICAMENT FOR PREVENTING THE TRANSMISSION OF HIV TO UNINFECTED CELLS AND CONTRACEPTIVE COMPOSITIONS COMPRISING THE SAID DERIVATIVES

Reference is made to and priority claimed from U.S. Provisional Application Ser. No. 60/018,668, filed May 30, 1996, entitled METHOD FOR PREVENTING THE TRANSMISSION OF HIV TO UNINFECTED CELLS, and U.S. Provisional Application Ser. No. 60/040,380, filed Mar. 10, 1997, entitled METHOD FOR PREVENTING THE TRANSMISSION OF HIV TO UNINFECTED CELLS.

FIELD OF THE INVENTION

This invention relates to a method for preventing or inhibiting the transmission of HIV to uninfected cells.

BACKGROUND OF THE INVENTION

Various compounds have been described as inhibitors of human immunodeficiency virus type 1 (HIV-1) in vitro hand are targeted at the virus-encoded reverse transcriptase (RT), e.g., nevirapine, pyridinone, TIBO, BHAP, TSAO, and quinoxaline. U.S. Pat. No. 5,268,389 describes certain thiocarboxylate ester compounds useful for inhibiting the replication of HIV. Copending U.S. patent application Ser. No. 08/565,493, filed on Nov. 30, 1995, describes certain methylfuranyl- and methylthienyl-pentenylether derivatives which are inhibitory of the replication of wild-type HIV-1 and HIV-1 reverse transcriptase mutant strains.

The currently approved drugs for the clinical treatment of HIV infection include the dideoxynucleosides AZT and 3TC, which inhibit the viral reverse transcriptase, and saquinavir, which inhibits the viral protease. These drugs are designed to be effective in patients already infected with HIV, in order to improve both the quality and extent of life of patients afflicted with this incurable disease.

However, there is a crucial need to identify therapeutic strategies that will minimize the spread of HIV from already-infected individuals to non-infected individuals. This includes the development of anti-HIV vaccines. Unfortunately, despite considerable effort and expense, this strategy has been so far unsuccessful.

Heterosexual contact is the primary mode of transmission of HIV infection worldwide. See Merson, M. H., Science 260: 1266–1268 (1993). Thus, a retrovirucidal spermicide or vaginal microbiocide could be an effective strategy to minimize the spread of HIV. So far, compounds considered as potential retrovirucides/vaginal microbiocides include virus envelop-disrupting agents, such as nonoxynol-9 [Roddy et al, Int. J. STD AIDS 4: 165–170 (1993), and inhibitors of HIV-CD4 receptor interaction, such as dextran sulfate [Mitsuya et al, Science 240: 646–649 (1988)] and modified β-lactoglobulin [Neurath et al, Nature Med. 2: 230–234 (1996)].

Pauwels and De Clercq, J. Acquired Immun. Def. Syndromes Hum Retrovirol. 11: 211–221 (1996) describe non-nucleoside inhibitors of HIV RT ("NNIRT") as potentially useful as retrovirucides/vaginal microbicides. The NNIRT typically are highly hydrophobic molecules, and thus readily traverse membrane barriers such as that surrounding the HIV core by passive diffusion. However, this property of NNIRT might also facilitate inhibitor efflux from the virion, in the absence of sufficient extra-virion levels of the NNIRT.

In order for the NNIRT to be a truly effective retrovirucide, the NNIRT should possess some property that will prolong its residence within the virion.

Ideally, retrovirucidal agents should fulfill several requirements. They should be effective directly on the virus. Retrovirucides should be effective at replication steps prior to integration of proviral DNA into the infected host cell genome. Although protease inhibitors prevent maturation of newly-produced virion particles, they are ineffective against pre-existing mature infectious HIV. Retrovirucides should be absorbable by uninfected cells, in order to provide a barrier to infection by residual active virus. Retrovirucides should be effective at non-cytotoxic concentrations readily attainable in vivo.

It is a purpose of this invention to provide a method to prevent or inhibit the transmission of HIV to uninfected cells whereby HIV infectivity is effectively inhibited or eliminated, by exposure of the virus or cells infected with the virus, to certain methylfuranyl- and methylthienyl-pentenylether derivatives, prior to contact with the uninfected cells. It is also the purpose of this invention to provide a method for treating uninfected cells with certain methylfuranyl- and methylthienyl-pentenylether derivatives to render the uninfected cells refractory to subsequent HIV infection.

SUMMARY OF THE INVENTION

This invention relates to a method for the prevention or inhibition of the transmission of HIV to susceptible uninfected cells by administering to the HIV or to cells infected with the HIV, an effective amount of a compound of the formula (I)

wherein X is O or S,
prior to the HIV or the cells infected with HIV, contacting the uninfected cells.

This invention relates to a method for preventing or inhibiting the transmission of HIV to susceptible uninfected cells by administering to the uninfected cells a prophylactically effective amount of a compound of the formula (I)

wherein X is O or S,
prior to the HIV or cells infected with HIV, contacting the uninfected cells.

This invention additionally relates to a contraceptive vehicle comprising a means for birth control and an HIV-protective amount of a compound of formula I.

DESCRIPTION OF THE FIGURES

FIG. 1 depicts the effect of preincubation of isolated HIV-1 with the indicated concentration of Compound IA(●)

or nevirapine (○) for 2 hours, on subsequent viral infectivity. Identical viral inocula (with respect to viral p24 levels) were then added to PHA-activated CBMC. Viral infectivity was assessed by measurement of RT activity in cell-free culture supernatants after 7 days incubation of cells and virus. (■) is a residual drug-effect control in which 0.5 μM Compound IA was carried through the dilution and concentration steps as for pretreated virus, then added to culture supernatants to test for effect on viral infectivity and possible inhibition of RT activity in the in vitro assay. The results are averages ±S.D. of triplicate determinations from three separate experiments.

FIG. 4A: Uninfected MT2 cells were incubated for 18 hours with varying concentrations of Compound IA in 1 ml media, then the cells were pelleted by centrifugation, and washed twice by resuspension in 10 ml medium followed by centrifugation. The cells were exposed to identical inocula of HIV-1 and cultured in the absence of added drug. Four days after removal of Compound IA, the extent of HIV-1 infection was assessed by measurement of syncytia formation (●), viral p24 antigen levels (▲), and RT activity (○), in cell-free supernatants. FIG. 4B: Concentration dependence of the Compound IA antiviral protective effect. Uninfected MT2 cells were incubated for 18 hours in the absence (○) or the presence of 0.5 μM (▲), 1 μM (▽), or 2 μM (●), of Compound IA. Residual exogenous drug was removed, and the cells were immediately exposed to identical inocula of HIV and cultured in the absence of added drug. The arrow indicates the addition of another aliquot of HIV-1 equivalent to that added to the cells at day 0. Viral cytopathicity was scored by microscopic assessment of syncytia formation. Data points are the averages of duplicate samples.

FIG. 5A: Uninfected MT2 cells were incubated for 18 hours in the absence (■) or the presence (●) of 2 μM of Compound IA, then the cells were isolated and cultured in the absence of drug. At various times thereafter, HIV-1 was added and virus infectivity assessed by microscopic analysis of syncytium formation. Data points are the averages of duplicate samples. FIG. 5B: Uninfected MT2 cells were incubated with 2 μM Compound IA for 10 minutes (●), 30 minutes (●), 60 minutes (□), or 120 minutes (▲), then the residual exogenous drug was removed and the cells were exposed to HIV-1. Virus infectivity was assessed by microscopic analysis of syncytium formation, and compared with infectivity of cells that had not been treated with the drug (●).

DESCRIPTION OF THE INVENTION

Preferably, this invention relates to a method for the prevention or inhibition of the transmission of HIV to susceptible uninfected cells by administering to the HIV or to cells infected with the HIV, an effective amount of a compound of the formula prior to the HIV or the cells infected with HIV, contacting the uninfected cells.

This invention also preferably relates to a method for the prevention or inhibition of the transmission of HIV to susceptible uninfected cells by administering to the uninfected cells a prophylactically effective amount of a compound of the formula prior to the HIV or cells infected with HIV, contacting the uninfected cells.

Preferably, the HIV-infected cells are HIV-infected cells in seminal fluid, vaginal fluid, or blood.

This invention preferably relates to a method for the prevention or inhibition of transmission of HIV in a human host in need thereof, which comprises administering by topical application to the human host in need thereof, an amount of the compound of formula I sufficient to exert a protective effect.

The compound is preferably administered topically to an uninfected individual in an area, such as the penis, vagina or rectum, which will be in contact with HIV or cells infected with HIV, prior to such contact. The compound can be topically administered in formulations comprising conventional acceptable carriers, adjuvants or vehicles, e.g., as a cream, gel, jelly, solution, ointment, and the like, using, conventional delivery systems, such as, e.g., a suppository, sponge, diaphragm, condom, vaginal douche, tampon, and the like.

The compound is also preferably topically administered to an HIV-infected individual in an area, such as the penis, vagina or rectum, which will be in contact with an uninfected individual and which is capable of transmitting HIV or cells infected with HIV to the uninfected individual, prior to such contact. The compound can be topically administered in formulations comprising conventional acceptable carriers, adjuvants or vehicles, such as, e.g., as a cream, gel, jelly, solution, ointment, and the like, using, conventional delivery systems, such as, e.g., a suppository, sponge, diaphragm, condom, vaginal douche, tampon, and the like.

Pharmaceutically acceptable carriers, adjuvants and vehicles useful in the composition of this invention can be found in standard pharmaceutical texts such as, e.g., *Remington's Pharmaceutical Sciences*, 16th Edition, Mack Publishing Company, Easton, Pa. (1980).

The methods of this invention can preferably be utilized as part of a prophylactic regimen designed to prevent, or protect against, possible HIV infection upon sexual contact with an infected individual. In this sense, one or more compounds of formula I can be formulated, e.g., into a creme, lotion, douche or into the lining of a condom.

The vaginal douches and cremes containing the compound of formula I can be of use in connection with presexual exposure protection. The cremes can, e.g., be mixed with nonoxynol-9 spermicide for use in conjunction with birth control, or added to condoms. In the case of vaginal sponges, e.g., containing the compounds of formula I, the compounds of formula I can be time-released over several hours with nonoxynol. The compounds can also be formulated in suppository forms for use during anal sex.

The prophylactically effective amount of the compounds useful in this invention that can be combined with the carrier to produce a single dosage form, will vary depending upon the host treated and the particular mode of administration. In general, the compounds of this invention are most desirably administered at a concentration level that will be sufficient to significantly inhibit or prevent HIV infection of cells in an uninfected individual on contact with an infected individual.

While the compounds of this invention can be administered as the sole active agents, the compounds can also be used in combination with one or more other agents which are not deleterious to the activity of the compounds of this invention or whose combination with the compounds will not have a deleterious effect on the host treated. For example, the compounds can be used in combination with other compounds that inhibit virus-cell interaction, such as modified β-lactoglobulin, or with compounds that disrupt the viral envelope membrane, such as nonoxynol-9.

In another embodiment of the method of this invention, the compound of formula I can be added to blood, blood by-products, or a blood preparation, in vitro. The compound can be added alone or in combination with a suitable vehicle. The effective amount required will depend upon a number of factors, including the particular blood preparation, and the vehicle chosen.

In further embodiments of the method of this invention, the compound of formula I can be added to disposable gloves used, e.g., by health care workers or researchers dealing with blood and bodily fluids, or to soap used in hospitals and research institutions.

Method of Synthesis

The compounds useful in the method of this invention can be prepared by reacting an acid of the formula A-COOH wherein A is with aniline derivative of the formula The acid, A—COOH, is first converted to its acid chloride and then treated with the aniline derivative and an acid scavenger, in a suitable solvent, to form an amide. The acid scavenger can be an organic base, such as pyridine, or an alkali metal hydroxide, carbonate or bicarbonate, such as sodium bicarbonate. Suitable solvents for this step include methylene chloride, diethyl ether, ethyl acetate, or the like. The resultant amide is then reacted with a thionylating agent such as, e.g., Lawesson's reagent or phosphorus pentasulfide, in the presence of an acid scavenger, e.g., pyridine or sodium bicarbonate, in an appropriate solvent. Heat is usually applied to complete the thionylation reaction. Suitable solvents for the thionylation reaction include toluene, xylene, DME, and the like.

[S] = Thionylating Agent

A second method for making the compounds of this invention is the metallation of a bromo compound of the formula A-Br with n-butyl lithium, at a temperature of −75° C. to −80° C. The resultant lithium complex is then reacted with an isothiocyanate of the formula The compounds useful in the method of this invention (carbothioamides) are then produced directly after acidification.

The following examples are provided to illustrate the present invention.

EXAMPLES

In the following examples, nevirapine, UC84, and Compound IA, have the following structures:

Materials and Methods

Compound IA

Compound IA was prepared as follows:

Step 1

Preparation of 2-Chloro-5-nitrophenol

2-Amino-5-nitrophenol (65.6 g) was added to 36% hydrochloric acid (200 mL) at 0 to 5° C. with stirring. A solution of sodium nitrite (33.25 g) in water (75 mL) was added dropwise over 1.5 hours, after which this first reaction mixture was held at this temperature for a further 1 hour. Excess nitrous acid was decomposed with sulfamic acid (1.5 g), added in portions. The first reaction mixture was then added in portions to a stirred suspension of copper (I) chloride (8.5 g) in 20% hydrochloric acid (50 mL). Considerable foaming occurred. After the addition, the resultant second reaction mixture was stirred for 1 hour. A precipitate from the second reaction mixture was then collected on a filter, washed with water and dried to give 63.2 g of brown solid. This solid was then refluxed with 1.5 g of activated carbon in methanol (500 mL) for 15 minutes; filtered through celite; and evaporated, to give 60.8 g of brown 2-chloro-5-nitrophenol.

Step 2

Preparation of 1-Chloro-2-(3-methyl-2-butenyloxy)-4-nitrobenzene

A reaction mixture of 2-chloro-5-nitrophenol (50.6 g), anhydrous potassium carbonate (44.5 g), tetrabutylammonium bromide (4.7 g) and 4-bromo-2-methyl-2-butene (53.3 g, 90%) in methyl ethyl ketone (263 mL) was stirred at ambient temperature overnight. TLC of the reaction mixture showed traces of phenol remaining. Additional prenyl bromide (1 mL) was then added to the reaction mixture and stirred for 2 hours. The solvent was then removed from the reaction mixture. The residue of the reaction mixture was then treated with water and extracted into diethyl ether. The extract was washed with 2N sodium hydroxide and water, dried (MgSO$_4$), filtered, and evaporated, to leave a brown solid which was recrystallised from ethyl acetate/isopropyl alcohol to give 1-chloro-2-(3-methyl-2-butenyloxy)-4-nitrobenzene, 49.5 g, a beige solid, a single spot on TLC (ethyl acetate:hexane, 20:80).

Step 3

Preparation of 4-Chloro-3-(3-methyl-2-butenyloxy)-benzenamine

To a refluxing well-stirred suspension of iron powder (19.6 g, 100 mesh) in ethanol (60 mL), water (13.4 mL) and 36% hydrochloric acid (1.4 mL) was added 1-chloro-2-(3-methyl-2-butenyloxy)-4-nitrobenzene (24 g) in portions over 15–30 minutes. After 3 hours thin-layer chromatography (TLC) (ethyl acetate:hexane, 40:60) showed no substrate. The reaction mixture was then filtered hot and the iron oxide filter cake was washed with hot ethanol. The combined ethanol washes were evaporated to produce a residue. The residue was taken up in diethyl ether, washed with aqueous bicarbonate and water, dried (MgSO$_4$), filtered, and evaporated, to give 4-chloro-3-(3-methyl-2-butenyloxy) benzenamine, 19.8 g of light brown oil.

Step 4

Preparation of 2-Methyl-3-furoyl Chloride

A first reaction mixture of chloroacetaldehyde dimethylacetal (300 g), water (400 mL) and 36% hydrochloric acid (40 mL) was stirred and brought to reflux. When the first reaction mixture became homogenous, it was cooled and added to a stirred solution of ethyl acetoacetate (260 g) and pyridine (500 mL) and left stirring at ambient temperature for 72 hours, to produce a second reaction mixture. The organic layer was then separated from the second reaction mixture and the aqueous layer was diluted with water and then extracted with methylene chloride. The combined organics were washed with 2N hydrochloric acid, followed by removal of the solvent. The residue was treated with a solution of sodium hydroxide (80 g) in water (700 mL) and ethanol (100 mL), to produce a third reaction mixture. After refluxing for 1 hour the third reaction mixture was poured into ice/water and acidified with hydrochloric acid. A cream colored precipitate formed. This precipitate was collected on a filter, washed with water and dried to give 2-methyl-3-furancarboxylic acid, 180 g. 100 g of the 2-methyl-3-furancarboxylic acid was added in portions to thionyl chloride (500 mL) and refluxed for 3 hours. Excess thionyl chloride was then distilled off to produce a residue. The residue was distilled using a water pump, to give 2-methyl-3-furanylcarboxylic chloride, bp. 62° C., 100 g.

Step 5
Preparation of N-[4-Chloro-3-(3-methyl-2-butenyloxy) phenyl]-2-methyl-3-furancarboxamide A first solution of 2-methyl-3-furancarboxylic chloride (13.57 g) in methylene chloride (94 mL) was stirred in an ice/salt bath. A second solution of 4-chloro-3-(3-methyl-2-butenyloxy)benzenamine (19.8 g), triethylamine (14 mL) in methylene chloride (94 mL) was added to the first solution at such a rate that the temperature was maintained at −5° C. to 0° C. When the addition was complete, the resultant reaction mixture was stirred to ambient temperature and left stirring for 15 hours. Water was added to the reaction mixture and then the organic layer separated and washed successively with water, dilute hydrochloric acid, water, aqueous sodium bicarbonate, and water. After drying ($MgSO_4$), the solvent was removed from the washed organic layer and the residue was recrystallised from isopropyl alcohol to give N-[4-chloro-3-(3-methyl-2-butenyloxy) phenyl-2-methyl-3-furancarboxamide, a white solid, 17 g. A second crop of beige crystals, 7.6 g, was also obtained.

Step 6
Preparation of N-[4-Chloro-3-(3-methy-2-butenyloxy)-phenyl]-2-methyl-3-furancarbothioamide (Compound IA)

A reaction mixture of N-[4-chloro-3-(3-methyl-2-butenyloxy)phenyl]-2-methyl-3-furancarboxamide (4 g), sodium bicarbonate (7.4 g) and Lawesson's reagent (3.6 g) in toluene (168 mL) was gradually heated to 85° C. over 1½ hours and then held at this temperature for a further 2½ hours. The reaction mixture was then cooled and filtered through a plug of neutral aluminum oxide and eluted with ether:petroleum ether (1:1). Evaporation of the solvent gave the product, N-[4-chloro-3-(3-methyl-2-butenyloxy) phenyl]-2-methyl-3-furancarbothioamide, 2.6 g.

Other Reagents

The following reagents were obtained from the NIH AIDS Research and Reference Reagent Program, Division of AIDS, NIAID:$HIV_{IIIb}$ laboratory strain of HIV-1, courtesy of Dr. R. C. Gallo; HXB2D infectious molecular clone of HIV-$1_{mb}$, courtesy of Drs. G. Shaw and B. Hahn. The CD4+ MT-2 and MT-4 cell lines were obtained from the American Type Culture Collection. UC84 and Compound IA were provided by Drs. W. A. Harrison and W. Brouwer, Uniroyal Chemical Ltd. Research Laboratories (Guelph, ON, Canada). Nevirapine was provided by Boehringer-Ingelheim Pharmaceuticals, Inc. (Ridgefield, Conn.). H9 cells chronically-infected with HIV ($HIV_{IIIb}$) were established in our laboratories. Cord blood mononuclear cells (CBMC) were isolated by Ficoll-Hypaque centrifugation from cord blood obtained from the Department of Obstetrics, SMBD-Jewish General Hospital. RPMI 1640 cell culture medium and heat-inactivated fetal bovine serum (FBS) were obtained from Canadian Life Technologies/GIBCO, Toronto, Canada. Centriprep-100 concentrating devices were a product of Amicon (Beverly, Mass.).

Cell Culture and Virous Replication

All cells were cultured in RPMI medium containing 10% fetal bovine serum. HIV-1 stocks were propagated by subculture in MT-2 cells; aliquots of the cell-free culture supernatants were generally used as viral inocula. In some cases, virus was further concentrated from these cell-free supernatants by ultracentrifugation. CBMC were prestimulated with phytohemagglutinin (PHA) prior to use in infection experiments, as described in Rooke et al, Virology 176: 205–215 (1990). Stock solutions of the test compounds were prepared in dimethyl sulfoxide (DMSO). Aliquots of the stock solutions were added to culture media immediately before use. The final concentration of DMSO in these working solutions was 1% or less. Control experiments showed that these concentrations of DMSO had no effect either on virus infectivity or on cell viability. Virus production was assessed by measurement of RT activity and viral p24 antigen levels in the culture supernatants. Cytopathic effects of HIV infection of CD4+ MT2 cells were also analyzed by microscopic assessment of syncytium formation as described in Yao et al, Virology 187: 56–62 (1992).

Example 1
Preincubation of Isolated HIV-1 With Test Compounds

HIV-1 ($TCID_{50}=5\times10^4$) was incubated in the absence or in the presence of varying concentrations of the test compounds (Compound IA and nevirapine), in a total volume of 1 ml RPMI in the absence of fetal bovine serum (FBS) for 2 hours at 37° C. with gentle agitation every 15 minutes. After incubation, drug-free RPMI was added to a final volume of 15 ml and the diluted sample was concentrated to a final volume of 0.7 ml using a Centriprep-100 centrifugal concentrating device, according to manufacturer's directions. The concentrated virus was diluted with drug-free RPMI to 10 ml and again concentrated to a final volume of 0.7 ml. Then 0.5 ml of this concentrated virus was then added to 0.5 ml of PHA-activated CBMC ($4\times10^6$ cells) in RPMI/10% FBS and incubated for 2 h at 37° C. with occasional gentle mixing. Residual test compound concentration at this stage was about 0.2% of that in the initial virus-test compound incubation. The HIV/CBMC incubation mix was diluted with the addition of 10 ml drug-free RPMI, and residual HIV was removed by pelleting the cells at 300×g for 10 minutes, followed by removal of the supernatant and resuspension of the cells in 2 ml RPMI/10% FBS containing IL-2 (10 U/ml). The entire sample was plated into a single well of a 24-well dish. After 4 days culture, 1 ml medium was removed and replaced with 1 ml of fresh medium. On day 7, culture supernatants were isolated and HIV production assessed by measurement of RT activity and p24 antigen levels in the cell-free supernatants. The results of this measurement are shown in FIG. 1.

Figure 1:
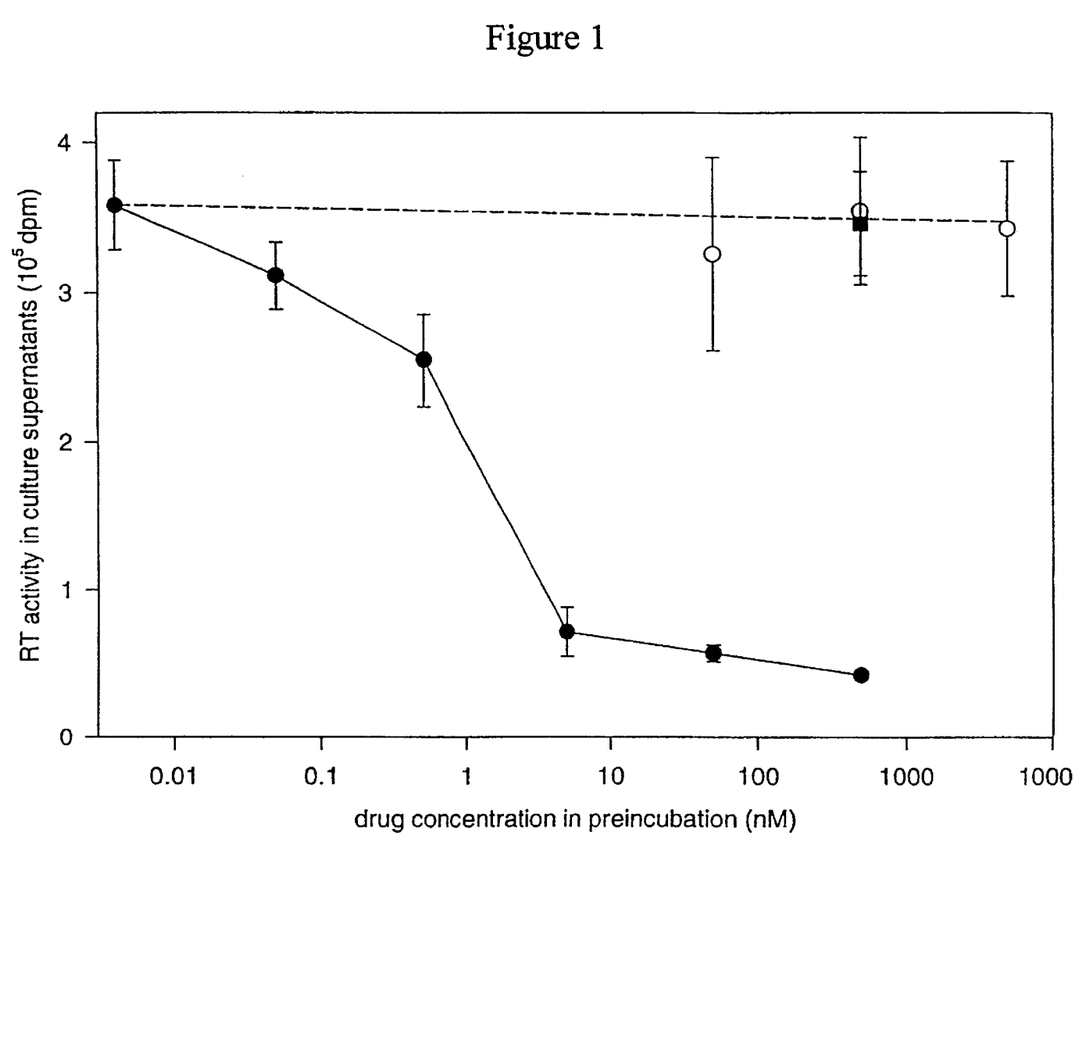

As can be seen from FIG. 1, virus was rendered non-infectious after a short incubation with Compound IA. No viral inactivation was noted with nevirapine.

Example 2
Incubation of HIV-1 Chronically-infected H9 Cells With Test Compounds

HIV-infected patient seminal and vaginal fluids contain not just free virus, but also virus-infected leukocytes. Levy, J. A., Microbiol. Rev. 52: 183–289 (1993). HIV-infected cells can be a significant source for viral transmissions in seminal fluids. Levy, supra and Pauwels et al, supra. Compound IA was examined for its effect on the infectivity of HIV produced from chronically-infected H9 cells, a T-cell lymphoma cell line.

Chronically-infected H9 cells ($5\times10^5$ cells) were incubated with varying concentrations of Compound IA in a total volume of 1 ml RPMI/10% FBS for 18 h at 37° C. The cells were then separated from the culture supernatants by centrifugation at 1000×g for 10 min. The virus particles were isolated from the culture supernatants and from residual Compound IA using Centriprep-100 centrifugal concentrating devices and the dilution/concentration protocol described above in Example 1. The pelleted H9 cells were washed by suspension in 10 ml RPMI, followed by centrifugation at 1000×g for 10 min. The cell pellet was resuspended in 4 ml RPMI/10% FBS, and used in co-culture experiments as described below.

Figure 2:
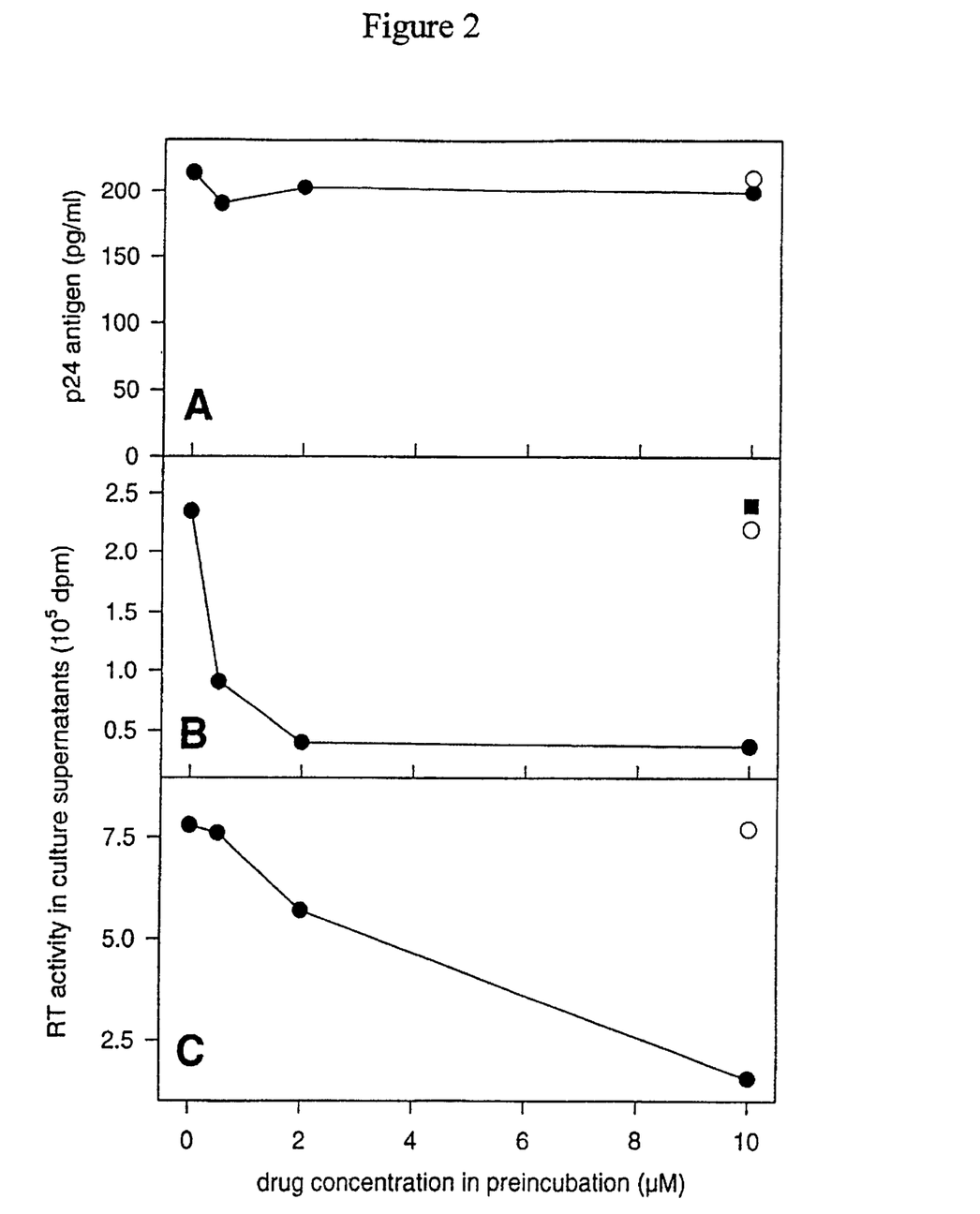
FIG. 2 depicts the effect of pretreatment of chronically-infected H9 cells with Compound IA or UC84 on (A) virus particle release from H9 cells during drug exposure, as assessed by measurement of HIV-1 p24 levels; (B) infectivity of isolated virus produced by H9 cells during drug treatment, as assessed by the ability to subsequently infect MT2 cells in the absence of drug; and (C) the ability of Compound IA-pretreated chronically-infected H9 cells to subsequently infect MT2 cells in co-culture experiments carried out in the absence of drug. The data illustrated for (B) and (C) were obtained four days after exposure of MT2 cells to virus or H9 cells, respectively. (○) Compound UC84; (●) Compound IA. (■) is a residual drug-effect control in which 10 μM Compound IA was carried through the dilution and concentration steps as for pretreated virus, then added to culture supernatants to test for effect on viral infectivity and possible inhibition of RT activity in the in vitro assay.

Aliquots of the final concentrated HIV suspension were added to MT-2 cells (3×10 cells/ml). Virus infectivity was assessed 6 days post-infection by analysis of syncytium formation, and RT activity and p24 antigen in the MT-2 cell culture supernatants. Similarly, aliquots of the drug-treated H9 cells were added to MT-2 cells (3×10$^5$ cells/ml) to give a final MT-2:H9 cell ratio of 30:1. Cells were co-cultured for 4 days, and HIV infection of MT-2 cells was scored by assessing syncytium formation and by analysis of RT activity in the culture supernatants. The results of this test are shown in FIG. 2.

Virus particles isolated after 24 exposure of the chronically-infected cells to Compound IA were significantly attenuated in infectivity. Additionally, virus produced by the H9 cells following removal of Compound IA were also attenuated in infectivity. This effect persisted for at least 4 days following removal of the extracellular Compound IA.

Example 3
Incubation of Peripheral Blood Lymphocytes (PBL) Cells With Compound IA and Nevirapine PBL cells (2×10$^6$ cells) isolated from blood of HIV-1 infected patients were incubated with media, 10 μM nevirapine and 10 μM Compound IA, in a total volume of 1 ml for 2 hr at 37° C. Excess drug was then removed by pelleting the cells by centrifugation at 300×g for 10 min and removal of the medium. The cell pellet was washed by suspension in 10 ml media, followed by centrifugation. This washing step was repeated twice. The final cell pellet was resuspended in 1 ml media, then co-cultured with 1 ml of activated CBMC (2×10$^6$ cells) The culture medium was changed every two days, and fresh activated CBMC (2×10$^6$ cells) were added once a week. HIV-1 production was monitored by measurement of p24 antigen levels in cell-free culture supernatants. The results of this testing are shown in FIG. 3.

Figure 3:
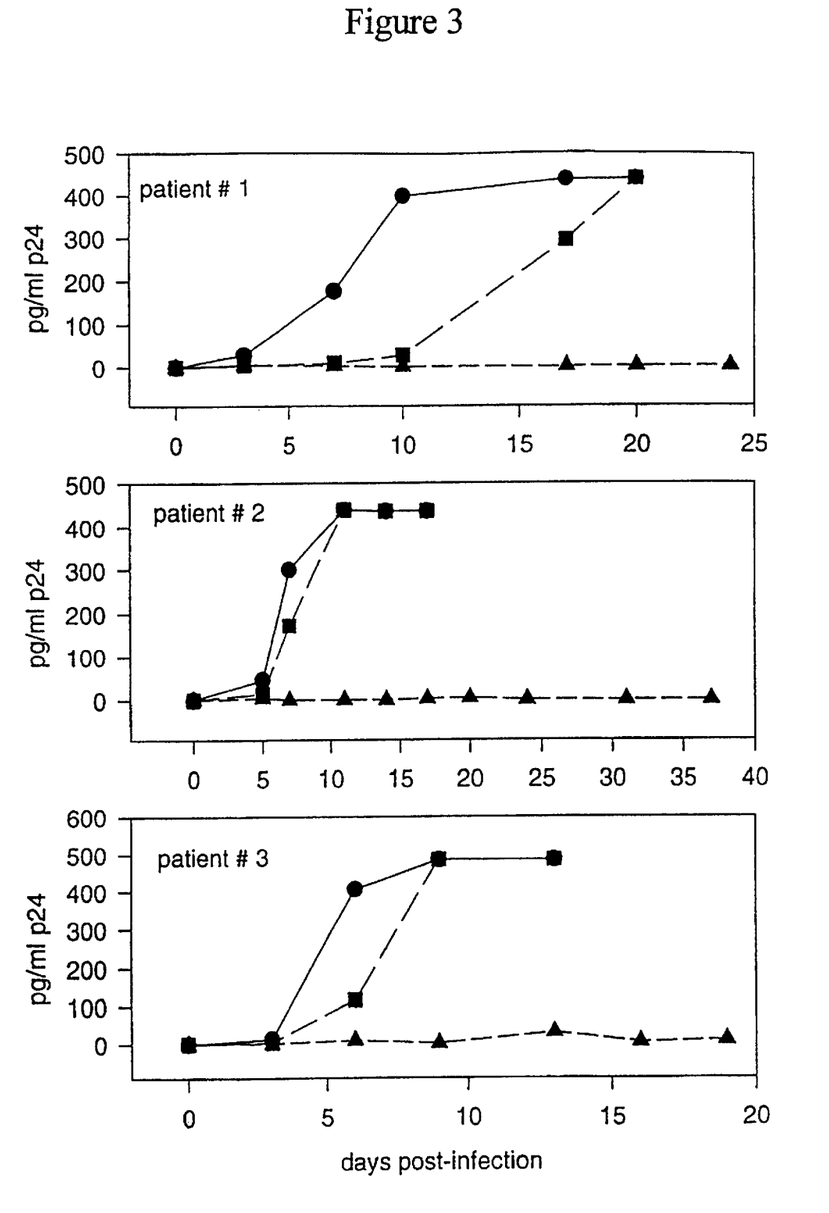
FIG. 3 depicts the effect of pretreatment of peripheral blood lymphocytes (PBL) from HIV-1 infected patients with Compound IA on the subsequent virus infectivity of CBMC cells. 2×10⁶ isolated PBL cells were incubated for 2 hours with media only (●), 10 μM nevirapine (■), or 10 μM Compound IA (▲), then residual drug was removed. The cells were then co-cultured with 2×10⁶ CBMC cells and p24 production was monitored.
Figure 4A:
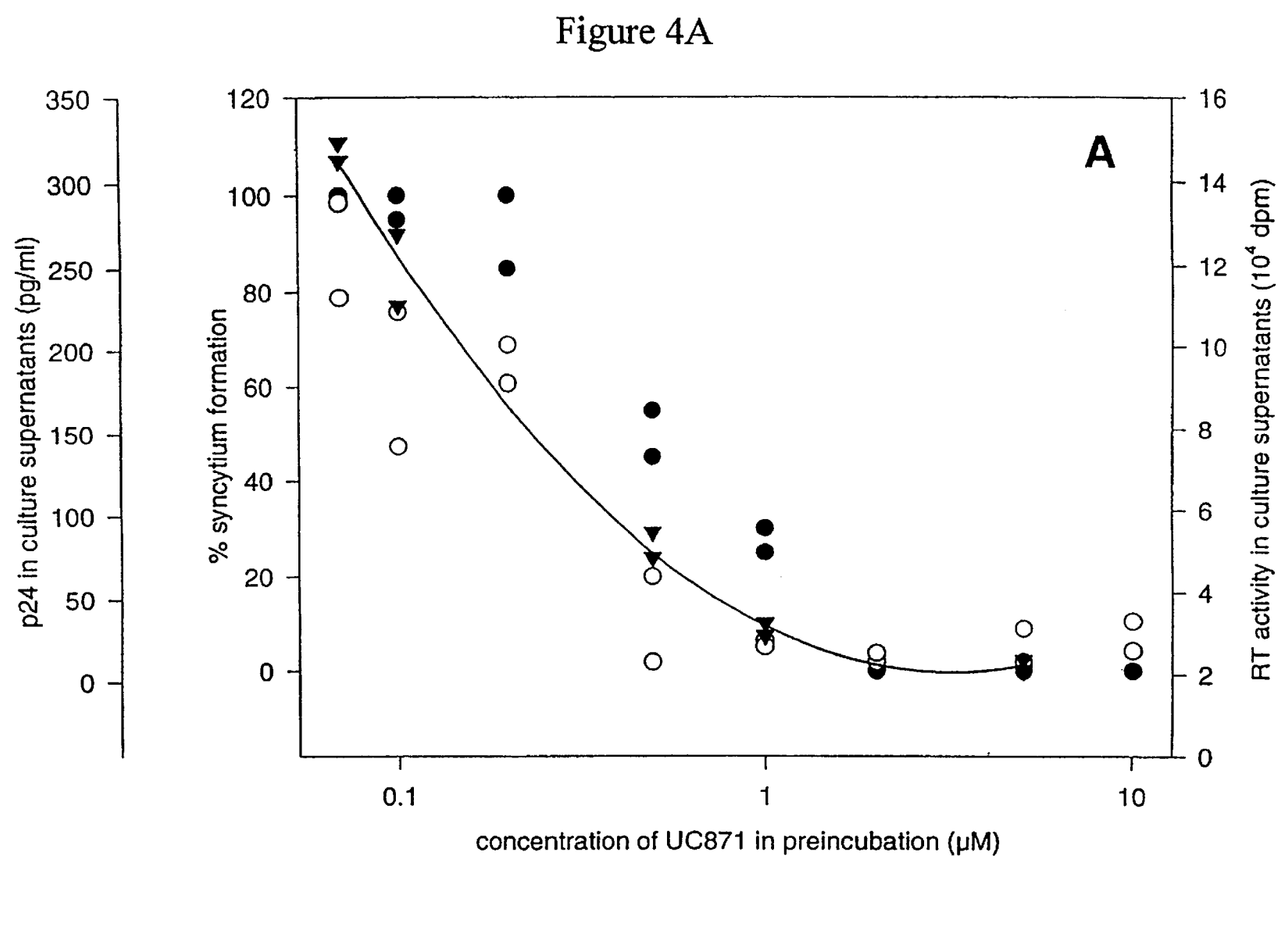
FIGS. 4A and 4B depict the effect of pretreatment of uninfected MT-2 cells with varying concentrations of Compound IA on the susceptibility of these cells to subsequent HIV infection in the absence of exogenous drug.
Figure 4B:
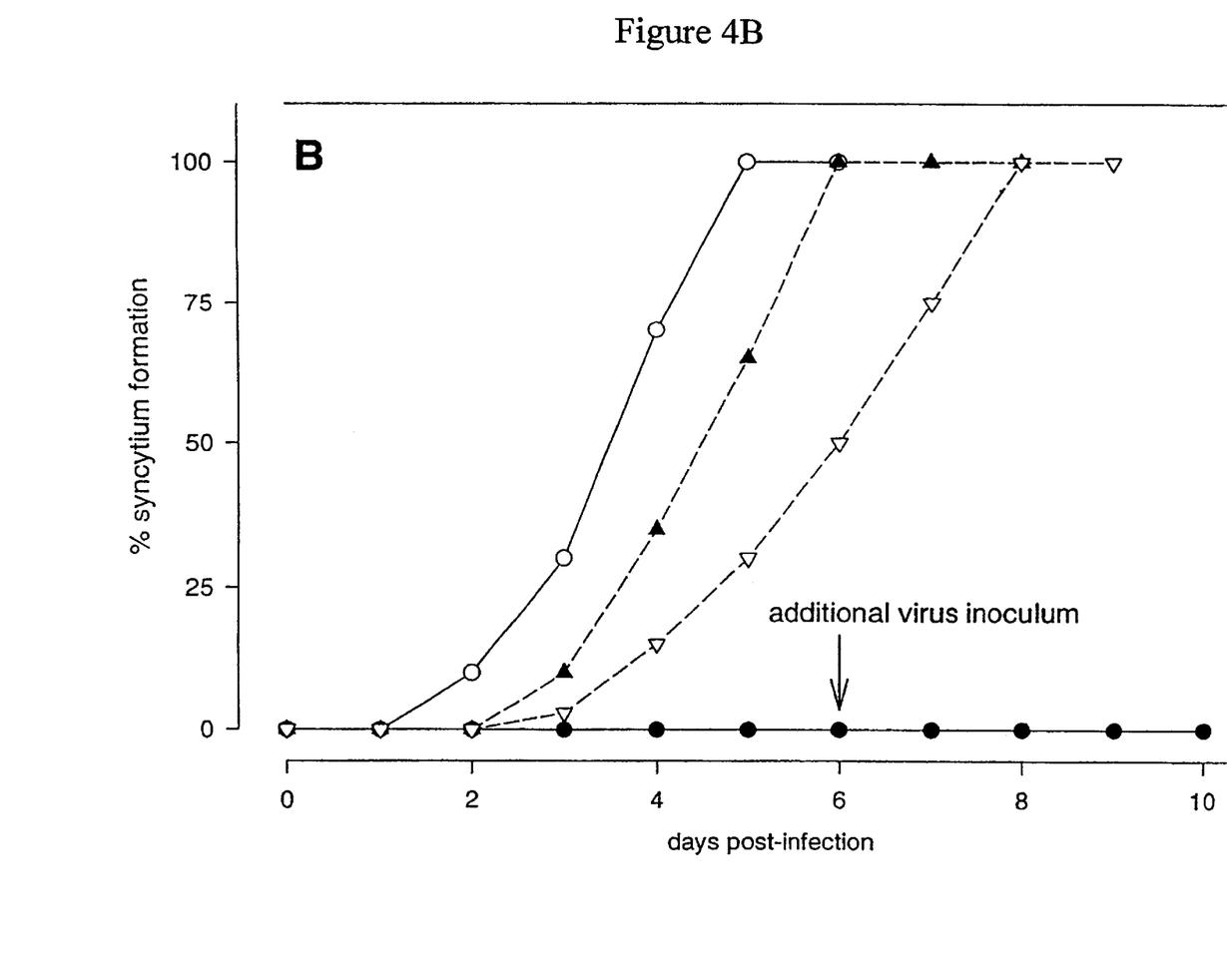
Figure 5A:
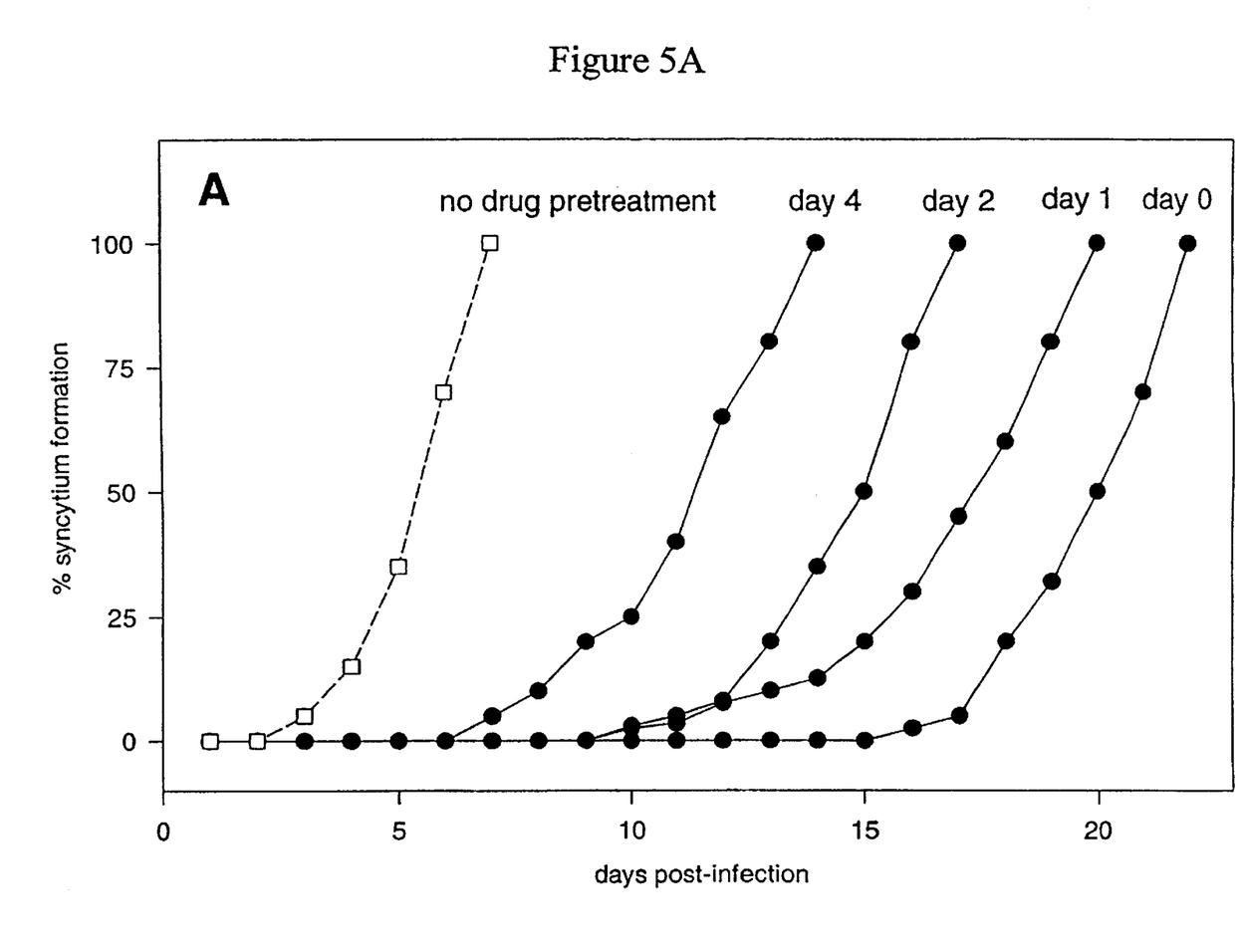
FIGS. 5A and 5B depict the time dependence of Compound IA antiviral protective effect.
Figure 5B:
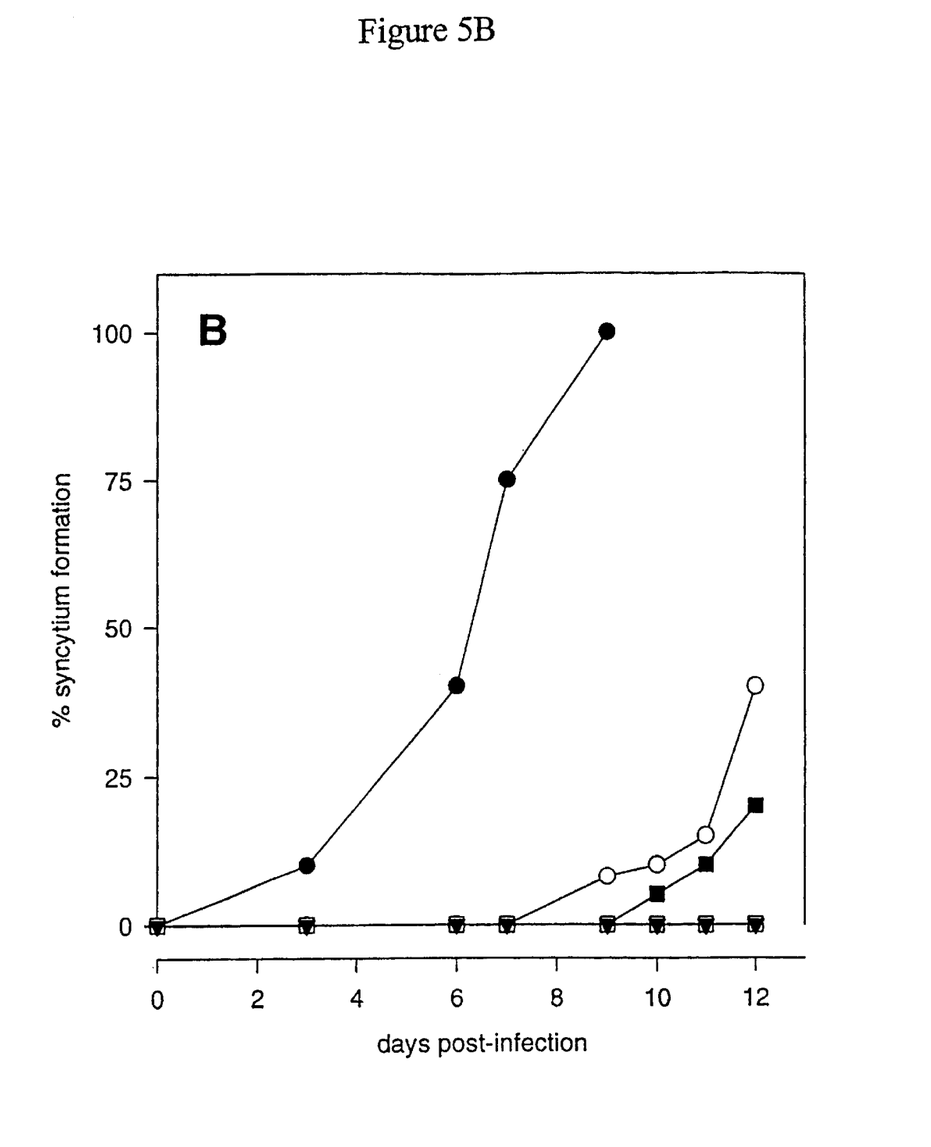

FIG. 3 illustrates the results obtained using PBL from three different patients.

As with the chronically-infected H9 cells, Compound IA abolished the infectivity of HIV-1 produced by the patient PBL. No viral infectivity was noted even after 30 days co-culture with uninfected CBMC. In contrast, nevirapine was unable to significantly delay viral infectivity.

Example 4
Effect of Pre-incubation of Uninfected MT-2 Cells With Test Compounds on Subsequent HIV Infection Uninfected MT-2 cells (2×10$^5$) were incubated in the absence or presence of varying concentrations of Compound IA in RPMI/10% FBS at 37° C. for various time periods ranging from 10 minutes up to 18 hours. After incubation with Compound IA, the cells were pelleted by centrifugation, and washed twice by resuspension in 10 ml medium followed by centrifugation, in order to ensure removal of residual exogenous Compound IA. The final cell pellet was resuspended with 1 ml media and an appropriate inoculum of HIV was added (TCID$_{50}$=5×10$^4$). Cells and virus were then incubated at 37° C. and the culture medium was changed every two or three days. Viral infection was scored by assessing the extent of syncytium formation at various times thereafter. The results of this test are shown in FIGS. 4A, 4B, 5A and 5B.

As can be seen in the figures, cells pretreated with 2 μM of Compound IA were completely resistant to the cytopathic effect of HIV-1 for at least 9 days, despite the continued presence of HIV-1.

What is claimed is:

1. A method for preventing or inhibiting the transmission of HIV to susceptible uninfected cells by administering to the HIV or to cells infected with HIV, an effective amount of a compound of the formula (I)

wherein X is O or S, prior to the HIV or the cells infected with HIV, contacting the uninfected cells.

2. The method of claim 1 wherein the compound is (IA)

3. The method of claim 1 wherein the compound is (IB)

4. The method as recited in claim 1 wherein the HIV or cells infected with HIV are in vaginal fluid, seminal fluid, or blood.

5. A method for preventing or inhibiting the transmission of HIV to susceptible uninfected cells by administering to the uninfected cells a prophylactically effective amount of a compound of the formula (I)

wherein X is O or S, prior to the HIV or cells infected with HIV, contacting the uninfected cells.

6. The method of claim 5 wherein the compound is (IA)

7. The method of claim 5 wherein the compound is (IB)

8. The method as recited in claim 5 wherein the uninfected cells are in the vagina, rectum, or blood.

9. The method as recited in claim 5 wherein the HIV or cells infected with HIV are in vaginal fluid, seminal fluid, or blood.

10. A method for the prevention or inhibition of transmission of HIV in a human host in need thereof, which comprises administering by topical application to the human host in need thereof, a protective amount of a compound of the formula (I)

wherein X is O or S.

11. A method as recited in claim 10 wherein the protective amount of the compound is topically applied to the vagina, penis or rectum of the human host.

12. The method of claim 10 wherein the compound is (IA)

13. The method of claim 10 wherein the compound is (IB)

14. A contraceptive vehicle comprising a means for birth control and an HIV-protective amount of a compound of the formula (I)

wherein X is O or S.

15. A contraceptive vehicle as recited in claim 14 wherein the vehicle is a condom, diaphragm or sponge.

16. A contraceptive vehicle as recited in claim 14 wherein the vehicle is a spermicide.

* * * * *